United States Patent [19]

Mita et al.

[11] Patent Number: 4,897,506

[45] Date of Patent: Jan. 30, 1990

[54] ISOLATION OF ALPHA-L-ASPARTYL-L-PHENYLALANINE METHYL ESTER FROM AQUEOUS MEDIUM

[75] Inventors: Ryuichi Mita, Omuta; Takeshi Oura, Zushi; Toshio Katoh, Kawasaki; Chojiro Higuchi; Akihiro Yamaguchi, both of Kamakura; Masanobu Ajioka, Yokohama, all of Japan

[73] Assignee: Mitsui Toatsu Chemicals, Incorporated, Tokyo, Japan

[21] Appl. No.: 256,838

[22] Filed: Oct. 12, 1988

[30] Foreign Application Priority Data

Oct. 13, 1987 [JP] Japan ................................ 62-256406
Jun. 7, 1988 [JP] Japan ................................ 63-138414

[51] Int. Cl.$^4$ ............................................ C07C 101/02
[52] U.S. Cl. ................................................... 560/41
[58] Field of Search ......................................... 560/41

[56] References Cited

U.S. PATENT DOCUMENTS

| | | | |
|---|---|---|---|
| 3,753,739 | 8/1973 | Cella et al. | 99/141 A |
| 3,761,288 | 9/1973 | Glicksman et al. | 99/141 A |
| 3,786,039 | 1/1974 | Ariyoshi et al. | 260/112.5 |
| 3,962,468 | 6/1976 | Pischke et al. | 476/96 |
| 3,971,857 | 7/1976 | Fruda et al. | 426/548 |
| 4,029,701 | 6/1977 | Haas et al. | 426/548 |
| 4,579,747 | 4/1986 | Sugiyama et al. | 426/548 |

FOREIGN PATENT DOCUMENTS

| | | |
|---|---|---|
| 0053844 | 6/1982 | European Pat. Off. . |
| 0088367 | 9/1983 | European Pat. Off. . |
| 59-177952 | 10/1983 | Japan . |

OTHER PUBLICATIONS

C. J. Hawkyard, "The Release of Disperse Dyes From Thickener Films During Thermal Processes", J. Soc. Dyes & Col. 97, 213, 214 (1981).

Kirk-Othmer's Encyclopedia of Chemical Technology (Third Ed.), vol. 20, pp. 216, 217.

*Primary Examiner*—Bruce Gray
*Attorney, Agent, or Firm*—Millen, White & Zelano

[57] ABSTRACT

A method for preparing α-L-aspartyl-L-phenylalanine methyl ester having improved solubilization by the isolation thereof from an aqueous medium containing at least one additive selected from the group consisting of sodium alginate, sodium salt of carboxymethylcellulose, sodium starch glycolate and sodium polyacrylate.

18 Claims, No Drawings

ISOLATION OF ALPHA-L-ASPARTYL-L-PHENYLALANINE METHYL ESTER FROM AQUEOUS MEDIUM

BACKGROUND OF THE INVENTION (a) Field of the Invention

The present invention relates to a method for the isolation from an aqueous medium of α-L-aspartyl-L-phenylalanine methyl ester (hereinafter abbreviated as α-APM) having a high rate of solution in water.

(b) Description of the Prior Art

α-APM is widely known as a dipeptide base sweetener. It has sweetness of good quality and a degree of sweetness about 200 times the sweetness of sucrose. The demand for α-APM as a diet sweetener is rapidly expanding.

α-APM is a dipeptide compound composed of L-aspartic acid and L-phenylalanine methyl ester. It can be prepared by both chemical and biochemical processes, the latter utilizing microorganisms. Various methods have been disclosed for each process.

As a typical example of a chemical process of producing α-APM, L-aspartic anhydride having a protected amino group is subjected to a condensation reaction with L-phenylalanine methyl ester in a suitable solvent and subsequently cleaving the protective group by a conventional method to obtain α-APM (For example, U.S. Pat. No. 3,786,039). In a representative biochemical process, N-benzyloxycarbonyl-L-aspartic acid and L-phenylalanine methyl ester are condensed in the presence of metalloprotease to obtain N-benzyloxycarbonyl-α-L-aspartyl-L-phenylalanine methyl ester. The benzyloxycarbonyl group is then removed from the intermediate by catalytic reduction to give α-APM.

In the industrial production of α-APM, a step of purifying crude α-APM is inevitable for the preparation of final product by isolating α-APM from the reaction mass, whichever of the above mentioned processes is employed. The purification step is usually carried out by recrystallization from a solution of water or a water-containing solvent (water or a water-containing solvent is hereinafter referred to as aqueous medium). Another method for removing impurities involves a stirring treatment of a suspension of α-APM in an aqueous medium, depending upon the quality of crude α-APM. However, pure α-APM obtained by this purification method forms a hard block in the dry state. Therefore, crushing is required for the preparation of final product, which causes difficulties in the handling of α-APM. Also, a long period of time is required for the drying and the content of a diketopiperazine compound, which is an intramolecular cyclization product of α-APM, is liable to increase. Thus the method causes problems in the manufacture of product having uniform quality.

α-APM purified by conventional recrystallization methods has the disadvantage of poor solubilization (rate of solution) in water. For example, when α-APM obtained conventionally by recrystallization from a 50 vol. % aqueous methanol solution is crushed and 250 mg of the resultant powder is poured into 250 ml of water with stirring at the room temperature and the solubilization thereof is determined by alternatively and repeatedly stirring and standing every 30 seconds, a significant amount of undissolved α-APM remains even after 5 minutes and more than 15 minutes is required for it to dissolve completely. α-APM obtained by recrystallization from water also has similar low solubilization.

Because the present demand for α-APM as a sweetener is primarily in the field of soft drinks, the solubilization of α-APM in water is definitely an important factor in the determination of product specifications. However, there is little prior art relating to improving the solubilization of α-APM itself.

Japanese Laid-Open Patent No. 177952/1983 discloses a method for crystallizing α-APM from an aqueous solution in which the initial concentration of α-APM is 2-10 wt. % and the aqueous solution is cooled with control of heat conduction and without providing forced flow, such as with mechanical stirring. The total mass is converted to a pseudo-solid phase having the consistency of a sherbet and, if necessary, further cooled. The thus-produced crystals of α-APM have enhanced filterability and the improved properties of fine particles, such as bulk density and the like. The α-APM thus-obtained is described as having excellent solubilization as compared to conventionally crystallized product. Although this method certainly improves various properties of the fine particles of α-APM thus isolated, including solubilization to a remarkable extent, because the crystallization from the aqueous solution is carried out by cooling without forced flow, such as mechanical stirring, conventional crystallizing equipment requires a remarkably long time for the cooling process to complete. This requires an increase in equipment scale and restricts its industrial application. Therefore, the patent specifies the maximum distance between the cooling surface and cooling zone and proposes that a special crystallization device be employed to meet this requirement. Thus, as a practical matter, the method of Japanese Laid-Open Patent No. 177952/1983 cannot be employed industrially without using the special crystallization device described therein.

The present inventors have extensively investigated this solubilization problem in order to develop an isolation method for the preparation of easily soluble pure α-APM under stirred conditions using conventional equipment fitted with a usual stirrer. They discovered that if the isolation of α-APM from an aqueous medium was conducted in the presence of a certain additive, as a result, the resultant α-APM has a remarkably improved solubilization (dissolution rate) in water as compared to α-APM isolated conventionally in the absence of additive.

SUMMARY OF THE INVENTION

The present invention is a method for the isolation of pure α-APM having improved solubilization which comprises isolating the α-APM from an aqueous medium containing at least one additive selected from the group consisting of sodium alginate, sodium salt of carboxymethylcellulose, sodium starch glycolate and sodium polyacrylate, which additive prevents the production of a form of α-APM which has poor solubilization when the α-APM is isolated conventionally from an aqueous medium.

DETAILED DESCRIPTION OF THE INVENTION

In the method of this invention, no specialized equipment is required and crystallization equipment fitted with conventional stirring means can be used. α-APM having a remarkably improved solubilization (solution rate in water) can be obtained by crystallizing the α-APM from the aqueous medium under stirring conditions or by a stirring treatment of a suspension of α-APM in the aqueous medium. Therefore, the method of this invention is industrially very valuable.

The α-APM used for the method of this invention may be of any purity but preferably is crude, e.g., about 95% or less purity, preferably 90–95%. The α-APM can be in the form of free amine or a mineral acid or sulfonic acid salt thereof. The starting α-APM is not restricted by the process for its preparation and α-APM prepared by various processes may be used as starting material for the method of this invention.

When a salt of α-APM is used, at least one additive selected from the group consisting of sodium alginate, sodium salt of carboxymethylcellulose, sodium starch glycolate and sodium polyacrylate can be added to a solution of the α-APM salt in an aqueous medium or to a solution thereof to which an inorganic base is added to adjust the pH of the solution to the isoelectric point of α-APM.

Salts of α-APM which can be used in the method of this invention include, for example, salts of mineral acids, such as hydrochloride, sulfate, phosphate and nitrate; and aliphatic and aromatic sulfonate salts, such as methane-sulfonate, ethanesulfonate, benzenesulfonate, p-toluenesulfonate, trifluoromethanesulfonate and naphthalenesulfonate. Preferred salts are hydrochloride, sulfate and methanesulfonate.

The aqueous medium used in the method of this invention is water or a mixture of water and a miscible organic solvent, e.g., usually water and a lower alcohol such as methanol, ethanol, isopropanol and tertiary butanol. Of course, other water miscible organic solvents may also be used, provided they do not adversely affect the object of this invention. When an aqueous medium containing a lower alcohol is used, the lower alcohol may be used to a concentration of about 60 wt. % without causing problems. Although the aqueous medium may be used in virtually any amount, it is usually used in the range of 3–50 times by weight of the —APM from a volume efficiency and workability standpoint.

The additive used in the method of this invention is a water soluble additive selected from the group consisting of sodium alginate, sodium salt of carboxymethylcellulose, sodium starch glycolate and sodium polyacrylate. The additive can be used singly or as a mixture of two or more thereof. When the amount of the additive is very small, the effect thereof on the solubilization of α-APM is not improved. On the other hand, too large an amount can adversely affect the separation between solid and liquid phases. Therefore, an amount thereof in the range of 0.01–3 wt. %, preferably 0.02–2 wt. %, based on the α-APM content of the starting material, is usually employed.

The additive can be added in solid form or used as a solution or colloidal suspension prepared in advance by dissolving the additive in water at the desired concentration. The additive should be completely dissolved in the aqueous medium.

The characterizing aspect of this invention is the separation of pure α-APM from an aqueous medium in the presence of an above-mentioned additive. In a preferred embodiment, the invention is conducted as part of a method of purifying crude α-APM. Alternatively, it may be employed as a post-treatment of purified α-APM, e.g., in the form of a wet cake thereof produced by the crystallization of crude α-APM from an aqueous medium in a conventional manner. Any type of treatment method can be used. For example, the method of this invention can comprise crystallizing α-APM from the aqueous medium or treating α-APM in a substantially suspended state in the aqueous medium. In the treatment of α-APM by crystallization, crude α-APM is preferably dissolved in the aqueous medium, any insoluble matter is filtered off and then the crystallizing operation is conducted under conventional stirring conditions. The above stated additive can be mixed with the α-APM prior to, during or after dissolving the α-APM. The object of this invention can also be achieved by incorporating the additive in the course of the crystallization or into the suspension of the α-APM in the aqueous medium after crystallization.

In the treatment method by crystallization, the preferred temperature for dissolving α-APM in the aqueous medium is usually not more than 70° C., because of the thermal stability of α-APM in solution at higher temperatures. When the solution is prepared at temperatures higher than 70° C., diketopiperazine compound is undesirably formed as by-product.

The solution of the crude α-APM may be used in any concentration, e.g., in the range of from 2 wt. % to saturation solubility at the dissolution temperature.

When the treatment of α-APM is conducted by stirring in the aqueous medium in a substantially suspended condition in the presence of above-mentioned additive, the aqueous medium may be used in any amount provided the α-APM forms a suspension therein. The temperature for the treatment may also be arbitrarily selected in the range of 0–60° C.

When a salt of α-APM is used as a raw material, the salt is dissolved in the aqueous medium, any insoluble matter is filtered off from the solution, and an inorganic base is added to the solution under usual stirring conditions, thereby adjusting the pH of the solution to the isoelectric point of α-APM, The above stated additive may be added to the solution in advance, in the course of, or after the pH adjustment.

The isoelectric point of α-APM is 5.6. The object of this invention can be achieved by adjusting the pH of the solution of the salt to the vicinity (within ±0.4) of the isoelectric point.

Examples of the inorganic base used in the method of this invention include sodium hydrogen carbonate, potassium hydrogen carbonate, sodium carbonate, potassium carbonate and aqueous ammonia.

The preferred temperature for dissolving the mineral acid and organic sulfonic acid salts of α-APM in the aqueous medium is not more than 50° C. because of the thermal instability in the solution of these salts at higher temperatures. The temperature is usually in the range of 25–30° C. When the solution is prepared at higher temperature than 50° C., diketopiperazine compound is undesirably formed.

The solution of the mineral acid and organic sulfonic acid salts of α-APM may be used in any concentration. The concentration may be arbitrarily selected in the range from 2 wt. % to the saturated solubility at the dissolution temperature.

The dry crystalline α-APM obtained by the method of this invention exhibits good solubilization in water. It does not dry into the hard blocks which are observed in the case of purification by a crystallization method. Thus, it is easy to process and use the dried α-APM.

Contemplated equivalents of the additives of this invention are other water soluble or colloidal dispersible gums and polymers which prevent the formation of α-APM having poor solubilization when it is isolated from an aqueous medium, e.g., other salts of alginic acid, carboxymethylcellulose, starch glycolic acid and polyarylic acid and other ingestibly acceptable polymeric materials.

The present invention is illustrated in detail by the examples which follow. The solubilization tests in the examples were carried out by the following method:

Method for Testing Solubilization:

Crushed α-APM sample (250 mg) is poured into 250 ml of purified water at 26±2° C. with stirring by a magnetic stirrer at 350- 360 rpm. Stirring and standing are alternately repeated for every 30 seconds and the time required for completely dissolving the sample is measured.

EXAMPLE 1

A mixture of 22 g of crude α-APM (95% purity) and 420 g of 40 vol. % aqueous methanol solution was warmed to 60° C. to dissolve the α-APM and then hot filtered to remove trace insoluble matter. To the resultant solution were added 10.0 g of a 1 wt. % aqueous solution of the sodium salt of carboxymethylcellulose. Crystallization was carried out by cooling with stirring. After cooling to 5° C., the separated crystals were filtered and washed with cold water.

The wet cake thus obtained was dried at 50-60° C. to give 17.8 g of purified α-APM. The purity thereof was 97.2% as determined by high performance liquid chromatography. The loss on drying was 3.2% after heating at 105° C. for 4 hours.

The solubilization test was conducted on the thus obtained αAPM. The sample was completely dissolved within 5 minutes.

EXAMPLE 2

A mixture of 22 g of crude α-APM (95% purity) and 80 g of 10 vol. % aqueous methanol solution was warmed to 62° C. to dissolve the crude α-APM and then hot filtered to remove a trace amount of insoluble matter. The resultant solution was cooled to 30° C. with stirring to crystallize the α-APM therefrom. Then 10.0 g of a 1 wt. % aqueous solution of the sodium salt of carboxymethylcellulose were added thereto.

The mixture was stirred for an hour at the same temperature and cooled to 5° C. The separated crystals were filtered, washed with a small amount of water and dried at 50-60° C. The yield was 17.6 g. The purity was 96.8%. The loss on drying was 3.6%.

The solubilization test was conducted on the thus obtained α-APM The sample was completely dissolved within 5 minutes.

COMPARATIVE EXAMPLE 1

Purification of the same crude α-APM by crystallization was carried out by the same procedures as described in Example 1 but without the addition of the sodium salt of carboxymethylcellulose.

The α-APM thus obtained had almost the same purity as that of Example 1. However, in the solubilization test, the sample required 12.5 minutes for complete dissolution.

COMPARATIVE EXAMPLE 2

Purification of the same crude α-APM by crystallization was carried out by the same procedures as described in Example 2 but without the addition of the sodium salt of carboxymethylcellulose.

The α-APM thus obtained had almost the same purity as that of Example 2. However, in the solubilization test, the sample require 11.5 minutes for complete dissolution.

EXAMPLE 3

A solution was prepared by dissolving 36.6 g of α-APM hydrochloride dihydrate in the 367.5 g of water at 25-30° C. and then filtered to remove a trace amount of insoluble matter. To the resultant solution were added 6.4 g of a 28% aqueous ammonia solution to adjust the pH to 5.6. Then 14.7 g of a 1 wt. % aqueous solution of the sodium salt of carboxy-methylcellulose was added.

After cooling the resultant mixture to 5° C. with stirring, the precipitated crystals were filtered and washed with cold water. The wet cake thus obtained was dried at 50-55 ° C. to give 27.9 g of α-APM. The product had a purity of 97.2%, as determined by high performance liquid chromatography. The loss on drying was 3.2% after heating at 105° C. for 4 hours.

Solubilization test was carried out on the crystals of α-APM thus obtained. The sample was completely dissolved within 5 minutes.

EXAMPLE 4

A mixture obtained by dissolving 39.2 g of α-APM sulfate in 420 g of water at 25-30° C. was filtered to remove trace insoluble matter. To the resultant solution were added 12.4 g of a 28% aqueous ammonia solution at the same temperature to adjust the pH to 5.6. Then 14.7 g of a 1 wt. % aqueous solution of the sodium salt of carboxymethylcellulose were added. The resultant mixture was stirred for an hour at the same temperature and cooled to 5° C. The separated crystals were filtered, washed with a small amount of cold water and dried at 50-55° C. The yield was 26.5 g. The purity was 97.0%. The loss on drying was 3.6% after heating at 105° C. for 4 hours.

The solubilization test was conducted on the α-APM thus obtained. The sample was completely dissolved within 5 minutes.

COMPARATIVE EXAMPLE 3

Purification of crude α-APM by crystallization was carried out by the same procedures as described in Example 3 but without the addition of the sodium salt of carboxymethylcellulose. The α-APM thus obtained had almost the same purity as that of Example 3. However, in the solubilization test, the sample required 12.5 minutes for complete dissolution.

COMPARATIVE EXAMPLE 4

5 Purification of crude α-APM by crystallization was carried out by the same procedures as described in Example 4 but without the addition of the sodium salt of carboxymethylcellulose. The α-APM thus obtained had almost the same purity as that of Example 4. However, in the solubilization test, the sample required 13.5 minutes for complete dissolution.

EXAMPLES 5-10 and Comparative Examples 5 and 6

22 g of crude α-APM (95% purity) was purified by recrystallization employing the general procedure of Example 1 but varying conditions such as the composition of the aqueous medium, the concentration of the α-APM in the aqueous medium and the amount and addition time of the sodium salt of carboxymethylcellulose, as shown in Table 1. The results obtained are summarized in Table 1.

room temperature. The separated crystals of α-APM were filtered, washed with a small amount of water and dried at 50–60° C.

The yield was 18.9 g. The purity was 97.0%. The loss on drying was 3.6%.

TABLE 1

Preparation of α-APM by crystallization and solubilization

| Example or Comparative Example | Aqueous Medium | α-APM concentration (wt. %) | Na—CMC* aqueous solution (1%) Amount (g) | Na—CMC* aqueous solution (1%) Addition time (Temperature) | Purified α-APM Yield (g) | Purified α-APM Solubilization (minutes) |
|---|---|---|---|---|---|---|
| Ex. 5 | 10 vol. % Methanol | 4.0 | 4.0 | in crystallization (25° C.) | 17.6 | 6.5 |
| Ex. 6 | water | 4.0 | 4.0 | in crystallization (25° C.) | 17.2 | 6.5 |
| Ex. 7 | 10 vol. Methanol | 4.0 | 20.0 | in crystallization (25° C.) | 17.7 | 4.5 |
| Ex. 8 | 30 vol. % Ethanol | 5.5 | 2.0 | in crystallization (60° C.) | 18.2 | 5.5 |
| Ex. 9 | 30 vol. % i-Propanol | 5.0 | 30.0 | in crystallization (20° C.) | 17.9 | 7.5 |
| Ex. 10 | Water | 4.0 | 4.0 | after crytallization (5° C.) | 17.0 | 5.5 |
| Comp. Ex. 5 | Water | 4.0 | — | — | 17.3 | 12.5 |
| Comp. Ex. 6 | 30% Ethanol | 5.5 | — | — | 18.4 | 13.5 |

*Sodium salt of carboxymethylcellulose

EXAMPLE 11

A mixture of 22 g of crude α-APM and 420 g of 40 vol. % aqueous methanol solution was warmed to 60° C. to dissolve the crude α-APM and then filtered to remove trace insolubles. The α-APM was crystallized from the resultant solution by cooling to 25° C. with stirring. To the crystal-containing mixture thus obtained were added 4.0 g of a 2% aqueous sodium alginate solution and stirring was continued for an hour at 25° C. The mixture was cooled to 5° C. and then suction filtered. The crystals were washed with a small amount of cold water and dried at 50–60° C.

The yield was 17.7 g. The purity was 96.8%. The loss on drying was 3.8%.

In the solubilization test, the sample completely dissolved in 6.5 minutes.

EXAMPLE 12

A mixture of 22 g of crude α-APM and 460 g of a 10 vol. % aqueous methanol solution was warmed to 60° C. to dissolve the crude α-APM and then filtered to remove trace insolubles. The resultant solution was subjected to crystallization by cooling to 25° C. with stirring. To the crystal containing mixture thus obtained were added 5.0 g of a 1% aqueous sodium starch glycolate solution and stirring was continued for an hour at 25° C. Then the mixture was cooled to 5° C. and suction filtered. The crystals of α-APM were washed with a small amount of water and dried at 50–60° C.

The yield was 17.8 g. The purity was 97.2%. The loss on drying was 3.4%.

In the solubilization test, the α-APM thus obtained was completely dissolved in 5.5 minutes.

EXAMPLE 13

A wet cake containing 22 g of conventionally obtained crystalline crude α-APM was poured into 180 g of water to which were then added 10 g of a 1 wt. % aqueous solution of the sodium salt of carboxymethylcellulose. The mixture was stirred for 2 hours at the room temperature. The separated crystals of α-APM were filtered, washed with a small amount of water and dried at 50–60° C.

The yield was 18.9 g. The purity was 97.0%. The loss on drying was 3.6%.

In the solubilization test, α-APM thus obtained was completely dissolved in 5.5. minutes.

COMPARATIVE EXAMPLE 7

The same procedures as described in Example 13 were carried out without the addition of sodium salt of carboxymethylcellulose.

The α-APM obtained had almost the same purity as that obtained in Example 13. However, in the solubilization test, the α-APM thus obtained required 13.5 minutes for complete dissolution.

EXAMPLE 14

A wet cake containing 22 g of α-APM was poured into 180 g of water and stirred for an hour at room temperature to give a uniform dispersion. Then 1.0 g of a 1 wt. % aqueous solution of the sodium salt of carboxymethylcellulose was added to the mixture and stirred for a further 2 hours. The separated crystals were filtered, washed with a small amount of water and dried at 50–60° C.

The yield was 18.7 g. The purity was 96.8%. The loss on drying was 3.8%.

In the solubilization test, the crystals of α-APM thus obtained were completely dissolved in 6.5 minutes.

EXAMPLE 15

The same procedures as described in Example 14 were carried out except that 4.0 g of a 1 wt. % aqueous sodium polyacrylate solution were added in place of the sodium salt of carboxymethylcellulose. The α-APM thus obtained had almost the same purity as that obtained in Example 14. In the solubilization test, the sample was completely dissolved in 5.5 minutes.

EXAMPLE 16

A solution was prepared by dissolving 16.6 g of α-APM hydrochloride dihydrate (95% purity) in 367.5 g of a 10 vol. % aqueous methanol solution at 25–30° C. and filtered to remove a trace amount of insoluble matter. Then 6.4 g of a 28% aqueous ammonia solution were added at 25–30° C. with stirring to adjust the pH of the solution to 5.6. To the solution thus obtained, were added 1.0 g of a 1 wt. % aqueous solution of the sodium salt of carboxymethylcellulose and then cooled to 5° C. with stirring. The separated crystals of α-APM were filtered and washed with cold water. The wet cake thus obtained was dried at 50–55° C. to obtain 27.5 g of α-APM. The purity was 97.2% based on high performance liquid chromatography analysis. The loss on drying was 3.2% after heating at 105° C. for 4 hours.

In the solubilization test, the α-APM thus obtained was completely dissolved within 5 minutes.

EXAMPLE 17

A solution was prepared by dissolving 36.6 g of α-APM hydrochloride dihydrate (95% purity) in 367.5 g of water at 25–30° C. and filtered to remove a trace amount of insoluble matter.

To the resultant solution, 6.4 g of a 28% aqueous ammonia solution were added at 25–30° C. with stirring to adjust the pH of the solution to 5.6. Then the solution was warmed to 55–60 ° C., stirred for an hour at the same temperature and then allowed to cool again to 25–30° C. with stirring. Subsequently, 2.9 g of a 1 wt. % aqueous solution of the sodium salt of carboxymethylcellulose were added and stirred for an hour at the same temperature. The separated crystals of α-APM were filtered and washed with a small amount of cold water. The wet cake obtained was dried at 50–60° C. to obtain 26.0 g of α-APM.

The purity was 97.2% based on high performance liquid chromatography analysis. The loss on drying was 3.2% after heating at 105° C. for 4 hours.

In the solubilization test, the crystals of α-APM thus obtained were completely dissolved within 5 minutes.

EXAMPLE 18

Purification of crude α-APM (95% purity) by crystallization was carried out by using the same procedures as described in Example 3 except that 8.8 g of sodium hydrogen carbonate were used.

The yield of purified α-APM was 27.0 g. Purity was 97.0%. The loss on drying was 3.6% after heating at 105° C. for 4 hours. In the solubilization test, the sample was completely dissolved within 5 minutes.

EXAMPLES 19-22

Purification of crude α-APM (95% purity) by crystallization was carried out by repeating the procedures described in Example 17 except that the additives and amount of water as shown in Table 2 were used. The results are summarized in Table 2.

EXAMPLE 23

Purification of crude α-APM (95% purity) by crystallization was carried out by the same procedures as described in Example 3 except that 39 g of α-APM methane sulfonate were used. The yield was 27.3 g. The purity was 97.1% as a result of analysis by high performance liquid chromatography. The loss on drying was 3.2% after heating at 105° C. for 4 hours. In the solubilization test, the crystals of α-APM thus obtained were completely dissolved within 5 minutes.

COMPARATIVE EXAMPLE 8

The isolation of α-APM was conducted by the same procedure as described in Example 13, except 10 g of sucrose fatty acid ester as a 0.5 wt. % aqueous solution was used as the additive. The α-APM obtained had almost the same purity as that obtained in Example 13. However, in the solubilization test, the α-APM thus obtained required 12.5 minutes for complete dissolution.

COMPARATIVE EXAMPLE 9

The isolation of α-APM was conducted by the same procedure as described in Example 13, except 0.3 g of sorbitan fatty acid ester as a 1 wt. % aqueous solution was used as the additive. The α-APM obtained had almost the same purity as that obtained in Example 13. However, in the solubilization test, the α-APM thus obtained required 12 minutes for complete dissolution.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method for the isolation of purified α-L-aspartyl-L-phenylalanine methyl ester (α-APM) wherein α-APM is separated from an admixture with an aqueous medium and then dried, the improvement which comprises dissolving in the aqueous medium, before separating the α-APM therefrom, at least one additive selected from the group consisting of sodium aligniate, sodium salt of carboxymethylcellulose, sodium starch glycolate and sodium polyacrylate, in an amount effective to produce isolated α-APM which when dried is readily soluble in water.

2. A method of claim 1, wherein the amount of the additive employed is 0.01–3% by weight of the α-APM.

3. A method of claim 1, wherein the α-APM in the starting mixture is produced by crystallization of crude α-APM from a solution thereof in the aqueous medium.

4. A method of claim 3, wherein the crude α-APM has a purity of about 95%.

5. A method of claim 1, wherein the starting mixture is produced by stirring a suspension of α-APM in the aqueous medium.

TABLE 2

| Example | Water (g) | Additive | α-APM Yield (g) | α-APM Purity (%) | α-APM Loss on drying (%) | α-APM Solubilization (min) |
|---|---|---|---|---|---|---|
| 19 | 264.6 | Sodium polyacrylate | 25.9 | 98.3 | 3.8 | 5.5 |
| 20 | 264.6 | Sodium starch glycolate | 26.0 | 98.2 | 3.7 | 5.5 |
| 21 | 264.6 | Sodium alginate | 25.8 | 98.4 | 3.1 | 5.5 |
| 22 | 264.6 | Sodium salt of carboxymethylcellulose | 25.9 | 98.2 | 3.7 | 5.0 |

6. A method of claim 5, wherein the α-APM used to produce the starting mixture is produced by mixing crude α-APM with the aqueous medium to produce a suspension thereof.

7. A method of claim 5, wherein the crude α-APM has a purity of about 95%.

8. A method of claim 1, wherein the starting mixture is produced by dissolving a mineral acid salt or an organic sulfonic acid salt of α-APM in the aqueous medium and then adjusting the pH of the solution with an inorganic base to the isoelectric point of the α-APM.

9. A method of claim 8, wherein the amount of additive employed is 0.01–3% by weight of α-APM.

10. A method of claim 8, wherein the starting salt of α-APM is crude and the α-APM is crystallized from the aqueous medium.

11. A method of claim 8, wherein the starting salt of α-APM is crude and a suspension of α-APM in the aqueous medium containing the additive is stirred.

12. A method of claim 1, wherein the additive is sodium alginate.

13. A method of claim 1, wherein the additive is sodium salt of carboxymethylcellulose.

14. A method of claim 1, wherein the additive is sodium starch glycolate.

15. A method of claim 1, wherein the additive is sodium polyacrylate.

16. A method of claim 1, wherein the aqueous medium is water or 10–40% aqueous methanol.

17. A method of claim 1, wherein the admixture of α-APM and the aqueous medium is produced by crystallization of crude α-APM from a solution thereof in an aqueous medium containing 0.02–2 wt. % of the additive, based on the α-APM; wherein the starting crude α-APM has a purity of about 95%; and wherein the aqueous medium is water or up to 10–40% aqueous methanol.

18. A method of claim 1, wherein the starting mixture is produced by stirring a suspension of α-APM in an aqueous medium containing 0.02–2 wt. % of the additive, based on the α-APM; wherein the starting mixture is produced by stirring a suspension of α-APM of a purity of about 95% in the aqueous medium and wherein the aqueous medium is water or up to 10–40% aqueous methanol.

* * * * *